US010444520B2

(12) United States Patent
Dholakia et al.

(10) Patent No.: US 10,444,520 B2
(45) Date of Patent: Oct. 15, 2019

(54) HIGH RESOLUTION IMAGING OF EXTENDED VOLUMES (71) Applicant: UNIVERSITY COURT OF THE UNIVERSITY OF ST ANDREWS, St Andrews (GB)

(72) Inventors: Kishan Dholakia, St Andrews (GB); Tom Vettenburg, St Andrews (BE)

(73) Assignee: UNIVERSITY COURT OF THE UNIVERSITY OF ST ANDREWS (GB)

( * ) Notice: Subject to any disclaimer, the term of this patent is extended or adjusted under 35 U.S.C. 154(b) by 1403 days.

(21) Appl. No.: 14/384,800

(22) PCT Filed: Mar. 26, 2013

(86) PCT No.: PCT/GB2013/050788
§ 371 (c)(1),
(2) Date: Sep. 12, 2014

(87) PCT Pub. No.: WO2013/150273
PCT Pub. Date: Oct. 10, 2013

(65) Prior Publication Data
US 2015/0029325 A1 Jan. 29, 2015

(30) Foreign Application Priority Data

Apr. 3, 2012 (GB) .................................. 1205974.7
Aug. 24, 2012 (GB) .................................. 1215169.2

(51) Int. Cl.
G01J 3/00 (2006.01)
G02B 27/09 (2006.01)
(Continued)

(52) U.S. Cl.
CPC ...... *G02B 27/0927* (2013.01); *G01N 21/6458* (2013.01); *G02B 21/0032* (2013.01); *G02B 21/10* (2013.01); *G02B 21/16* (2013.01); *G02B 21/367* (2013.01); *G02B 27/0944* (2013.01); *G02B 27/0988* (2013.01); *G02B 27/58* (2013.01); *G02F 1/01* (2013.01); *H04N 7/18* (2013.01); *G01N 21/65* (2013.01)

(58) Field of Classification Search
CPC ...... G01J 3/02; G01J 3/28; G01J 3/42; G01N 21/31; G01N 21/552
USPC .......................................................... 356/300
See application file for complete search history.

(56) References Cited

U.S. PATENT DOCUMENTS 7,609,391 B2 * 10/2009 Betzig ................ G01N 21/6445
356/457
2009/0073563 A1 * 3/2009 Betzig ................ G01N 21/6445
359/578

FOREIGN PATENT DOCUMENTS

WO  WO 2012/003259 A1  1/2012

OTHER PUBLICATIONS

International Search Report prepared by the European Patent Office dated Jun. 10, 2013, for International Application No. PCT/GB2013/050788.
(Continued)

Primary Examiner — Md M Rahman
(74) Attorney, Agent, or Firm — Sheridan Ross P.C.

(57) ABSTRACT

A light sheet optical system comprising means for forming a light sheet using a non-diffractive or quasi non-diffractive and/or propagation invariant beam that has an asymmetric intensity beam profile transverse to the direction of propagation, such as an Airy beam.

22 Claims, 6 Drawing Sheets (51) Int. Cl.
G01N 21/64 (2006.01)
G02B 21/10 (2006.01)
G02B 21/16 (2006.01)
G02B 21/36 (2006.01)
G02B 27/58 (2006.01)
G02B 21/00 (2006.01)
G02F 1/01 (2006.01)
H04N 7/18 (2006.01)
G01N 21/65 (2006.01)

(56) References Cited

OTHER PUBLICATIONS

Written Opinion prepared by the European Patent Office dated Jun. 10, 2013, for International Application No. PCT/GB2013/050788.
Search Report prepared by the Great Britain Intellectual Property Office dated Aug. 6, 2012, for Great Britain Application No. GB1205974.7.

Fahrbach et al: "Microscopy with self-reconstructing beams", Nature Photonics, vol. 4, No. 11, Sep. 12, 2010 (Sep. 12, 2010), pp. 780-785.
Broky et al: "Self-healing properties of optical Airy beams", Optics Express, vol. 16, No. 17, Aug. 18, 2008 (Aug. 18, 2008), p. 12880.
Hwang et al: "Kessel-like beam generation by superposing multiple Airy beams", Optics Express, vol. 19, No. 8, Apr. 11, 2011 (Apr. 11, 2011), p. 7356.
Mazilu et al: "Light beats the spread: "non-diffracting" beams", Laser & Photonics Reviews, vol. 4, No. 4, Jun. 25, 2010 (Jun. 25, 2010), pp. 529-547.
Baumgartl et al: "Optically mediated particle clearing using Airy wavepackets", Nature Photonics; vol. 2, Nov. 2008, pp. 675-678.
Siviloglou et al: "Observation of Accelerating Airy Beams", Physical review Letters, PRL 99, 213901-1 to 213901-4 (2007).
Davis et al: "Observation of accelerating parabolic beams", Optics Express, vol. 16, No. 17, pp. 12866-12871, 2008.
Berry et al: "Nonspreading wave packets", American Journal of Physics 47, 264 (1979); View online: http://dx.doi.org/10.1119/1.11855.

* cited by examiner

HIGH RESOLUTION IMAGING OF EXTENDED VOLUMES

CROSS REFERENCE TO RELATED APPLICATIONS

This application is a national stage application under 35 U.S.C. 371 and claims the benefit of PCT Application No. PCT/GB2013/50788 having an international filing date of Mar. 26, 2013, which designated the United States, which PCT application claimed the benefit of Great Britain Application No. 1205974.7 filed Apr. 3, 2012, and Great Britain Application No. 1215169.2 filed Aug. 24, 2012, the disclosure of each of which are incorporated herein by reference in their entirety.

FIELD OF THE INVENTION

The present invention relates to a method and system for high resolution imaging of extended volumes.

BACKGROUND OF THE INVENTION

Applications of volumetric imaging can be found in all sectors of society from healthcare, to manufacturing, basic research, and defence. More often than not, current technology limits the acquisition volume and resolution that can be captured in a given time frame. Taking the example of optical microscopy, confocal scanning was until recently the gold standard, yet its acquisition time is limited by the scanning speed which in turn is limited by the laser power and the damage threshold of the sample. Various forms of light sheet microscopy such as orthogonal-plane optical sectioning, selective plane illumination microscopy (SPIM), uitramicroscopy, or digital scanned laser sheet microscopy (DSLM), address this issue. Unwanted background signal and photo-damage is prevented by illuminating the to-be-imaged volume in a stepwise fashion while rapidly capturing as much information as possible from the illuminated parts, e.g. using an adequately placed detector array such as a charge-coupled device camera (CCD). With its various implementations, this technique enables rapid high contrast four-dimensional optical sectioning, and has already revolutionised the study of live organisms.

A problem with conventional light sheet microscopy, based on Gaussian beams, is that high isotropic resolution demands a tightly focussed light sheet and therefore illumination with a high numerical aperture (NA). However, this restricts the distance over which a narrowly focussed light sheet can be maintained, thereby limiting the usable field-of-view. The ability to efficiently image large volumes with a single scan of a standard Gaussian light sheet is therefore incompatible with high resolution imaging.

Imaging large volumes at maximal resolution is key to many areas of research such as imaging for biological studies, whether this be archaebacteria, prokaryotes or eukaryotes and at the subcellular, cellular, tissue and in the whole organism level. Examples include embryology, cell-fate mapping both in stem cells studies and in developmental biology, neurobiology, cell spheroids. High resolution imaging of large volumes may also be used in the area of colloidal physics, and for imaging nanostructures such as three-dimensional meta-materials.

Several solutions have been proposed. Generally these are either restricted to two-photon excitation or require a larger number of sample exposures with the associated consequences for imaging speed and photo-damage that may hamper repeated scans. Bessel beams have been used to extend the imaging volume in light sheet microscopy. The transverse intensity profile of a zeroth Bessel order beam has a central spot and a series of concentric rings away from the beam centre. These rings significantly deteriorate the axial resolution.

Confocal detection of the Bessel beam core can improve the axial resolution. However, its advantage over regular confocal microscopy is small since a significant fraction of the light is rejected by the confocal detection of the light sheet beam, and the scanning speed is limited by the camera because images are acquired line-by-line instead of plane-by-plane. Whilst previous work has shown that the scan volume can be extended by using propagation-invariant, non-diffracting Bessel beams, for single photon excitation the trade-off is a significant loss in signal to noise ratio and resolving power achievable at irradiation levels compatible with biological imaging.

SUMMARY OF THE INVENTION

The present invention provides a means to create a light sheet with an asymmetric intensity profile in the scan direction, e.g. the squared Airy function. Such a light sheet may be non-planar and can be used for optical manipulation or for high resolution imaging of extended volumes. The asymmetric light sheet may be created from a non-diffractive, propagation invariant beam, defined here as any beam that maintains approximately the same intensity profile in the plane transverse to its propagation direction. The profile may translate or accelerate transversely to the propagation direction. The non-diffractive nature of the light sheet of the invention can be used to extend the field-of-view, and thus imaging volume of light sheet microscopy.

The use of an asymmetric light sheet enables high resolution throughout the entire imaging volume. Perfectly non-diffractive, propagation invariant beams exist only in theory. However, adequate quasi-non-diffractive approximations of such beams exist that still allow a significant extension of the field-of-view. For example, an asymmetric Airy beam, readily generated with a Fourier transform of a cubic phase modulation, is able to extend the field-of-view by an order of magnitude, whilst maintaining high isotropic resolution.

Alternatively, the asymmetric and/or propagation invariant light sheet can be created from any symmetric light sheet by modulating the illumination path after the generation of the light sheet. The position of the modulating element can be placed at any convenient place in the illumination path, be incorporated in any of its optical components, the illuminating objective, the light sheet generating element, or form part of the laser source. An asymmetric intensity profile may also be created by time-modulating the intensity of a symmetric and/or propagation invariant light sheet whilst scanning it transverse to the propagation direction.

The light sheet optical system of the invention can be configured for use as a light sheet imaging system and/or a light sheet spectroscopy system, for example a Raman spectroscopy system, and/or a light sheet microscopy system and/or a light sheet system for exerting an optical force on a particle, such as any inert or biological particle or cell, for example an optical trapping system or an optical guiding system.

The term 'light sheet' is used in the description of the invention in the generic sense of an illumination or irradiation pattern or set of patterns. The term 'light sheet microscopy' or 'light sheet imaging' is used independently of how the 'light sheet' is projected into the volume or how information is collected from the irradiated part(s), even if this is not necessarily at the microscopic scale.

Preferably, the propagation-invariant, non-diffractive asymmetric beam has self-healing properties, i.e. the beam can repair itself after passing obstacles (see for example "Optically mediated particle clearing using Airy wavepackets" by Baumgartl et al Nature Photonics, 2, November 2008). Ideally, the beam should have no or a minimal number of zeros for low spatial frequencies in its modulation transfer function (MTF).

The light sheet has an asymmetric transverse intensity profile such as the squared Airy function. The propagation-invariant, non-diffractive asymmetric field may have a Fourier transform that includes a phase term which has a second or higher order component, for example a third or higher order component, in its polynomial Taylor expansion. The Airy beam for example has a cubic phase term in its Fourier transform. Symmetric intensity profiles would have a real optical transfer function that under defocus will become oscillatory and go through zero. Such zeros represent an irretrievable loss of image information and thereby limit the field-of-view of symmetric light sheets. In contrast, any asymmetric profile yields a complex-valued optical transfer function, making it extremely unlikely that both the real and imaginary parts are simultaneously zero, even if the transfer function becomes oscillatory under defocus.

When used for imaging, the light sheet of the invention can increase the field-of-view devoid of MTF zeros, thereby preserving as much information as possible. The recorded image sequence does not need to be sharp and can look blurred to the human observer. If it contains the necessary information, sharp images can be reconstructed by digital means such as a simple, one-dimensional, linear deconvolution, typically handled in real time. The additional freedom given by this hybrid optical-digital approach can be leveraged to design the light sheet so that the quality of the final, processed, image is maximized. The image deconvolution step is only necessary when acquiring images for a human observer. Machine vision applications, such as the automated inspection of samples, may skip the image deconvolution step and obtain the desired information directly from the recorded data.

According to one embodiment of the invention, there is provided a light sheet microscope for imaging a volume comprising means for forming a light sheet using a propagation-invariant, non-diffractive asymmetric beam, such as an Airy beam. Although multi-photon excitation light sheet microscopy may benefit from asymmetric beams, preferably single photon excitation is used.

Using an Airy beam for light sheet imaging provides high resolution for single photon excitation and over a large field-of-view. Only a single exposure per image section is required; however, a set of neighbouring recorded image sections contains information about each two-dimensional slice of the reconstructed image volume. Optimal sharpness is therefore only obtained by using digital deconvolution. The technique enables, for example, specimens at sub-cellular resolution to be studied, whilst providing a holistic view of the interactions. The linear character of this technique facilitates its extension beyond fluorescence imaging to other imaging modalities such scattering and spectroscopy such as Raman imaging and coherent anti-Stokes Raman scattering (CARS).

An Airy wavepacket has been shown theoretically by Berry, M. V. & Balazs, N. L. Nonspreading wave packets. Am. J. Phys. 47, 264-267 (1979) to be a "diffraction-free" solution to the Schrodinger equation for a free particle. In the absence of any external potential the wavepacket may freely accelerate transverse to its propagation direction. The mathematical analogy between the Schrodinger equation and the paraxial wave equations may be used to realise finite energy Airy beams in the optical domain as recently witnessed, see Siviloglou, G. A., Broky, J., Dogariu, A. & Christodoulides, D. N. "Observation of Accelerating Airy Beams" Phys. Rev. Left. 99, 213901 (2007). The beam has the form of a central maximum and a number of side lobes that exhibit transverse motion.

Counter-intuitively, an Airy beam has an acceleration transverse to its propagation direction associated with its light field [Berry, M. V. & Balazs, N. L. Nonspreading wave packets Am. J. Phys., 47, 264-267 (1979)]. Particle trajectories may be induced to follow parabolic trajectories, commensurate with that transverse acceleration, As well as Airy beam(s), other parabolic beams, or appropriate combinations of beamsbeam arraysscanned beams may be used. Examples of parabolic beams are described in Davis, J. A. et al, Observation of accelerating parabolic beams. Opt. Express 16, 12866-12871 (2008).

The asymmetric light sheet of the invention may be formed using any form of static or dynamic refractive, reflective, or diffractive optical element or the beam can be emitted directly from a specialised laser. Dynamic modulation with for example a spatial light modulator offers the additional advantage that the light sheet can be corrected for system or sample induced aberrations; however, static modulation can be achieved at low cost in the form of a transmissive or reflective optical element with the appropriate surface/refractive index modulation or diffraction grating. The modulating element may perform multiple functions, e.g. it may be integrated into the light sheet generating element, the laser, a lens, or any other component that is irradiated.

Means may be provided for moving or positioning the asymmetric light sheet to capture images at different positions throughout a sample volume, and to ensure that the focal plane of the detection objective is well located with respect to the asymmetric beam light sheet.

The light sheet may consist of multiple light surfaces, formed by the transverse structure of the light sheet, from which information can be collected in parallel using a detector array. Multiple surfaces may be formed by the side lobes of an asymmetric light sheet such as that created from the Airy light sheet.

To aid in the alignment, a second objective and detector may be placed in the path of the light sheet on the illumination axis.

Although the light sheet of choice may be curved, this is not a requirement for extending the field-of-view of the imaging system. However, the curving may be used to apply optical 'bending' forces to microscopic objects.

BRIEF DESCRIPTION OF THE DRAWINGS

Various aspects of the invention will now be described by way of example only and with reference to the accompanying drawings, of which.

DETAILED DESCRIPTION OF THE DRAWINGS

Figure 1:
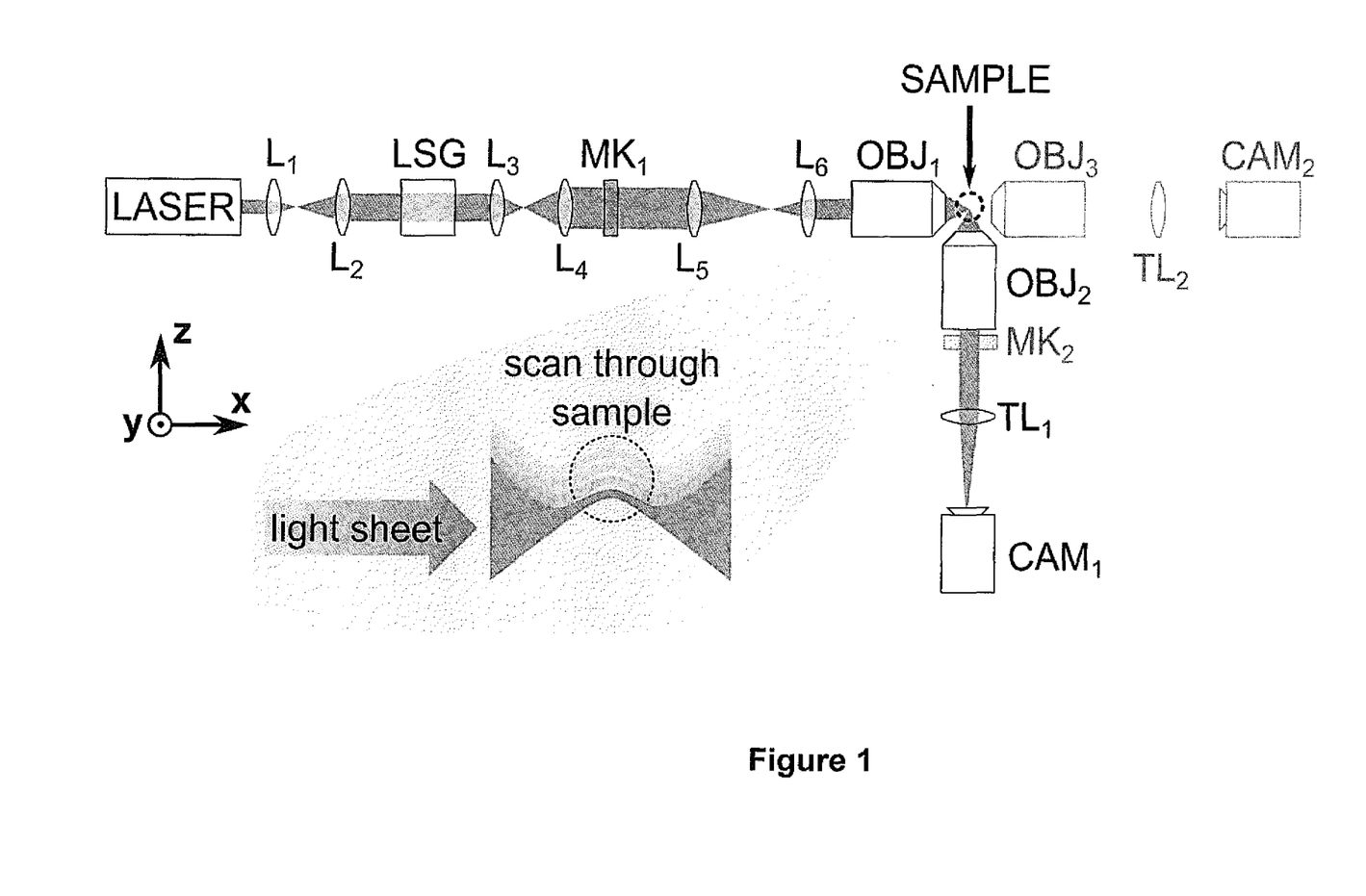
FIG. 1 shows a simple schematic of an Airy beam light sheet microscope.

FIG. 1 is a simple schematic of the principles of operation of a light sheet microscope. This shows the illumination propagation direction (x), the direction in which the beam is expanded to form the light sheet (y), and the detection axis (z). A detector placed along the z-axis records a sequence of images from illuminated 'planes' while the light sheet is displaced with respect to the sample.

The output beam of a laser passes through lenses $L_1$ and $L_2$ and is converted into a light sheet with a light sheet generating element (LSG), which can be a cylindrical lens or a scanning device such as an acousto-optical deflector (AOD). Lenses $L_1$ and $L_2$ adjust the beam for the LSG diameter. The beam is then passed through lenses $L_3$ and $L_4$ and shaped into an imaging volume extending light sheet with the aid of mask, $MK_1$. This may be a static or dynamic spatial light modulator (SLM) that may be removable or switchable. This modulation may be introduced at any point in the illumination path, before, after, or integrated with other optical elements such as the light sheet generating element. In this specific configuration, lenses $L_3$ and $L_4$ adjust the beam to the size of mask $MK_1$. Lenses $L_5$ and $L_6$ adjust the beam output from mask $MK_1$ to an objective lens $OBJ_1$.

Light transmitted via the spatial light modulator $M_1$ illuminates the sample, and is focussed by objective lens $OBJ_1$ into a specific sample region. An image stack of the sample is captured using the same, or a second objective lens $OBJ_2$ and camera ($CAM_1$). Optionally, a third objective lens $OBJ_3$ and a second camera ($CAM_2$), can be used for calibration of the system. Tube lenses ($TL_1$ and $TL_2$) may be used to focus the light coming from the objectives ($OBJ_2$ and $OBJ_3$) onto the active area of the cameras ($CAM_1$ and $CAM_2$), respectively. The mask, $MK_1$, creates a beam such as the Airy beam, which is quasi non-diffractive, i.e. propagation invariant, and self healing. This permits an extension of the imaging volume along the x-axis by at least an order of magnitude with respect to that achievable with the conventional Gaussian light sheet.

An optional mask $MK_2$, can be inserted at or near the back aperture of the second objective lens $OBJ_2$ to increase the depth of field of the detection path, thereby facilitating the alignment and which may lead to a reduction in manufacturing costs. Additional optical elements could also intentionally introduce focal plane curvature to improve the coincidence of the detection focus with the light sheet.

Figure 2:
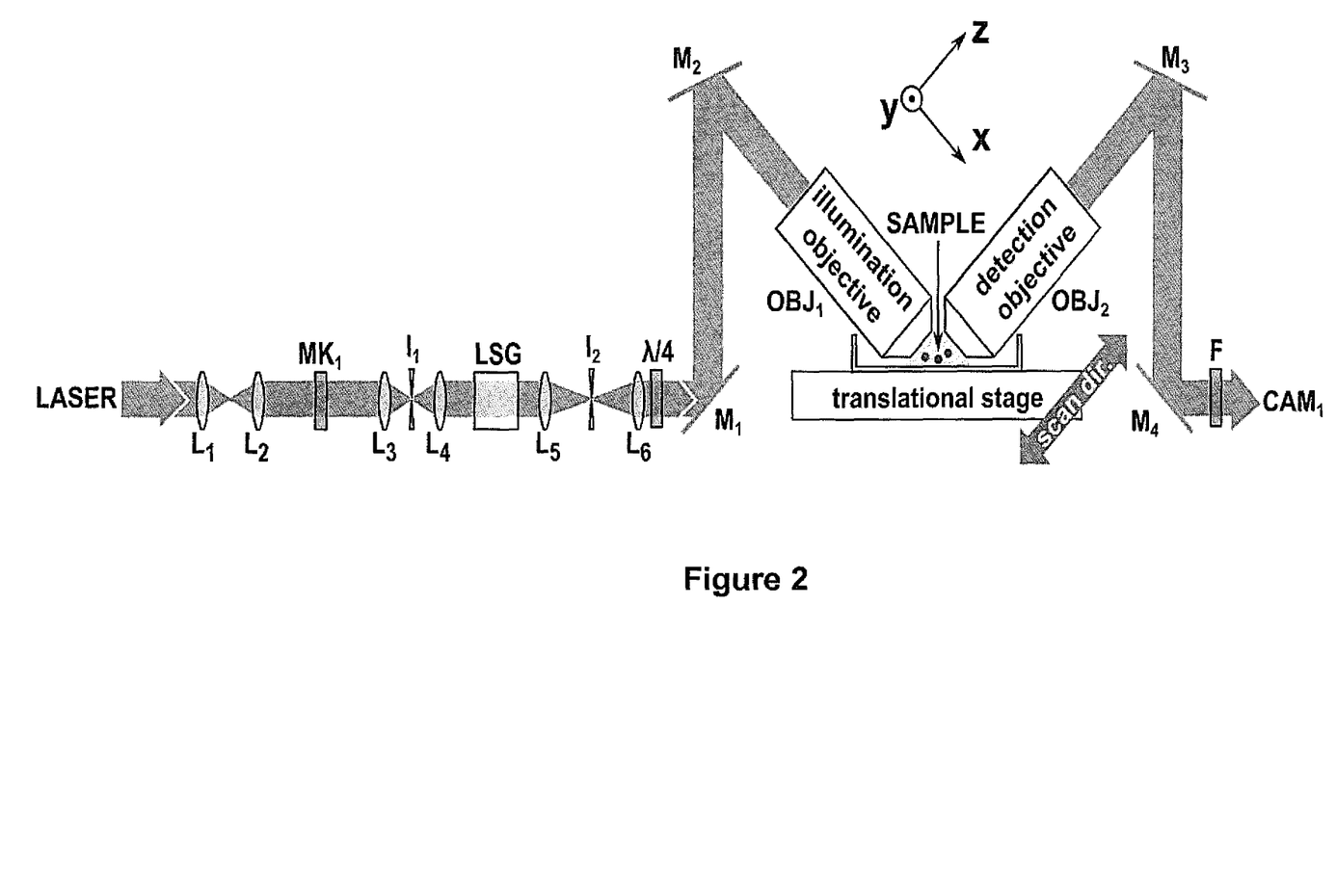
FIG. 2 exemplifies an alternative geometry of the Airy beam light sheet microscope with several optional elements.

FIG. 2 depicts a schematic of an alternative geometry that permits imaging water immersed samples on a horizontal surface such as a standard microscope slide or dish. This is enabled by positioning illumination and detection objectives at 45 degrees to the horizontal sample stage as shown in FIG. 2. By translating the sample diagonally as indicated by the "scan dir." arrow, a three dimensional volumetric image can be recorded as previously described for FIG. 1.

More specifically, FIG. 2 shows a laser emitting a light beam that is expanded by lenses $L_1$ and $L_2$ to match mask $MK_1$ (mask $MK_2$ is not used in this example). As before, the mask may be a static or dynamic spatial light modulator (SLM) that may be removable or switchable. Having passed through the mask $MK_1$, the beam is then passed through a lens $L_3$, where is it focussed onto an iris $I_1$ and through another lens $L_4$, where it is shaped to the diameter of a light sheet generating element (LSG). The LSG can be a cylindrical lens or a scanning device such as an acousto-optical deflector (AOD). The light sheet that is formed by the LSG is then passed through a lens $L_5$, where is it focussed onto an iris $I_2$ and through another lens $L_6$, which collimates the light sheet onto a quarter wave plate, which provides polarization control. From there, the light sheet is reflected from a first mirror $M_1$ onto a second mirror $M_2$ and from there onto an illumination objective $OBJ_1$, which is positioned at 45 degrees to the horizontal sample stage. Light that has passed through a sample on the stage passes through a detection objective $OBJ_2$ onto a third mirror $M_3$ and from there onto a fourth mirror $M_4$, where it is directed to a camera $CAM_1$.

The mirrors $M_1$ to $M_4$ can be used to facilitate the vertical alignment of the objectives with the sample. In one example, mirrors $M_2$ and $M_3$ can be fixed with respect to the axis of the objectives $OBJ_1$ and $OBJ_2$, respectively. Appropriate alignment of mirrors $M_1$ and $M_4$ allows a vertical translation of both objectives $OBJ_1$ and $OBJ_2$ and mirrors $M_2$ and $M_3$ with respect to the sample stage without altering the alignment. Axial translation stages on the objectives may facilitate fine-tuning the alignment.

The illumination path of FIG. 2 is a variation of that shown in FIG. 1. Various optional elements are included to control the polarization and to filter the light. The different order of $MK_1$ and LSG in FIGS. 1 and 2 demonstrates that the order of many optical elements can be rearranged. Optional irises, $I_1$ and $I_2$, in FIG. 2 select the first diffraction orders to allow more flexibility and prevent unwanted illumination of the sample. As in FIG. 1, lenses $L_1$ to $L_6$ form telescopes to relay the light between the various components. An optional polarization control element, $\lambda/4$, can be introduced to control the polarization of the light, e.g. by converting linear polarized light to circularly polarized light that produces a more uniform excitation of fluorescence. Light filters, F, e.g. to block excitation light and select fluorescence emission, can be introduced between $OBJ_2$ and the camera, CAW. If necessary or convenient, elements of the illumination path and the detection path can be brought closer than the mirrors to $OBJ_1$ and $OBJ_2$, respectively.

Figure 3:
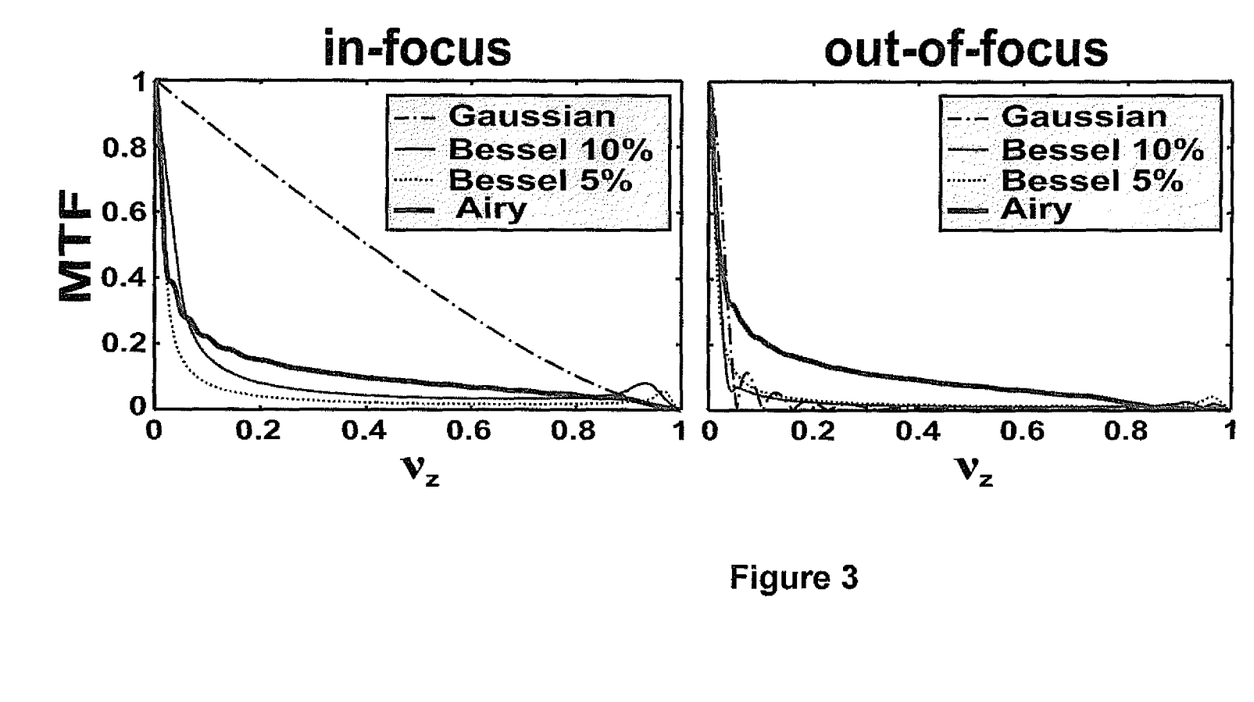
FIG. 3 show the modulation transfer function for different light sheet types.

FIG. 3: To assess the performance of various beam types for light sheet microscopy, a study of modulation transfer function (MTF) has been performed. Relative fringe contrast as a function of spatial frequency, given by the MTF, provides insight into the relationship between contrast and resolution for various illumination types. The MTF is calculated as the absolute value of the optical transfer function, defined here as the Fourier transform of a z-axis section of the normalised light sheet intensity. FIG. 3 shows the MTF for various types of light sheet, (a) at the illumination focal position, and (b) at an out-of-focus plane (x=25 μm). The spatial frequency ($v_z$), is normalised to the highest transmitted spatial frequency: $2NA/\lambda$, where $\lambda$ and NA are, respectively, the illumination wavelength and the numerical aperture. Two approximations of the Bessel beam are compared: 'Bessel 10%' and 'Bessel 5%', which are generated using annular apertures with a relative open fraction of the radius of 10% and 5%, respectively.

FIG. 3(a) shows that the MTF of an apertured Gaussian provides the highest contrast at light sheet waist (black dash dotted line). However, as can be seen from FIG. 3(b) the contrast drops significantly and even has many zero values away from the light sheet waist. The traditional aperture Gaussian light sheet is therefore only valuable near the light sheet waist. The Bessel and Airy beams show much less variation in and out of focus, and hence are not restricted to imaging near the light sheet waist, yielding the associated field-of-view enhancement. However, the MTF of the Bessel beams (solid blue and dotted red line) is significantly lower than that associated with the Airy beam (solid green line). Moreover, the Bessel beam with the smaller open fraction of 5% shows a proportional reduction in contrast, ultimately limiting the resolution that can be achieved in practice; moreover, it can be shown that the contrast converges to zero for the theoretical Bessel beam. This is unfortunate, because Bessel beams generated with the narrowest annuli yield the largest field-of-view. In general large field-of-view can only be obtained with the Bessel beam light sheet by trading off resolution. The Airy beam is free of such a restrictive trade-off. Due to the asymmetry of the Airy beam, its transfer function is not strictly real and has a spatial frequency dependent complex argument. The complex character of the transfer function makes it very unlikely that the defocus induced changes cause its real and imaginary parts to become zero simultaneously. By consequence, for asymmetric beams, low MTF values only occur for large defocus and at high spatial frequencies. Unlike the significant contrast reduction associated with the Bessel beam, a phase shift does not affect the signal to noise ratio and hence can be readily accounted for by a simple linear deconvolution.

An Airy beam maintains its transverse intensity profile during propagation, to some extent even in the presence of obstacles such as scatterers ('self-healing or self-repairing'). As it has side-lobes and follows a parabolic trajectory, the Airy beam might not appear appealing for light sheet imaging. However, in practice, it has been found that using propagation-invariant, non-diffractive Airy beam extends the effective field-of-view for light sheet imaging by at least and order of magnitude beyond that achievable using the conventional apertured Gaussian beam.

Converting a conventional light sheet microscope into an Airy light sheet microscope could be done by simply incorporating a cubic phase modulation, e.g. using a piece of transparent material with spatially varying optical thickness, in the illumination path of a conventional light sheet microscope. Mathematically the cubic phase modulation can be written as $\alpha(u_y^3+u_z^3)$, where $\alpha$ is a parameter that permits tuning the propagation invariance of the light sheet to match the required field-of-view, while $u_y$ and $u_z$ are normalised Cartesian coordinates aligned with the y and the z-axis respectively. it would be possible to make the Airy beam light sheet planar by orienting the mask so that the Airy beam curve remains in the plane of the light sheet. Since the point-spread function is formed by time-averaging the beam intensity in the y direction, the light sheet MTF is a section through the origin of the two-dimensional MTF of the Airy beam. It can be calculated that a mask rotation of 45 degrees to keep the propagation path within the light sheet plane would reduce the contrast to practically zero at a low spatial frequency. This should not be entirely surprising since, although an asymmetric beam is used to create the light sheet, the light sheet itself would be symmetric due to the time averaging along the y-axis.

Various experiments have been conducted to test the effectiveness of an Airy beam for light sheet microscopy (or any of its various implementations) in comparison to other beam types. In these experiments, a conventional laser beam (Coherent Verdi V6, 6W 532 nm) was expanded to fill the aperture of an acousto-optical deflector (AOD, Neos AOBD 45035-3) and create the light sheet by scanning the laser focus along the y-axis with a period of 2 s, considerably shorter than the shortest acquisition time (840 s). Next, the AOD aperture was re-imaged using a magnifying telescope to overfill the active area of a spatial light modulator (SLM, Hamamatsu LCOS X10468-04). The use of an SLM enabled rapid dynamic switching between the various light sheet types under investigation and allowed data cubes to be recorded for the various beam types in parallel, minimising the influence of photo bleaching and sample movement. This permitted the elimination of residual aberrations in the system, ensuring that the beams closely resemble the theoretical descriptions.

The active area of the SLM was imaged onto the back aperture of the illumination objective (Mitutoyo 20×/0.42, working distance 20 mm), using a demagnifying telescope (0.5×) with a slit aperture at its focus to select the first diffraction order. The beam was focussed inside the sample, held in a square-profile borosilicate glass capillary (Vitrocell 8250-100, 1 mm side, wall thickness 200 μm). The capillary was filled with fluorescent polystyrene beads (Duke R900) immobilised in PDMS, and mounted on an xyz-piezo stage (Mad City Labs, Nano-LP200) to allow automatic positioning of the sample with respect to the light sheet and the focal plane of the detection objective.

Fluorescence was detected using a CCD camera (Basler piA640-210gm) via an orthogonally mounted objective (Newport 20×/0.40) with appropriate tube lens and fluorescence filter. Note that an orthogonally positioned objective is typical, however, other configurations may be more convenient such as slanted illumination through the detection lens or otherwise positioned secondary lens or waveguide. The light sheets were scanned through the sample in steps of 100 nm using a combination of piezo-stage translation and holographic deflection with the SLM.

Figure 6:
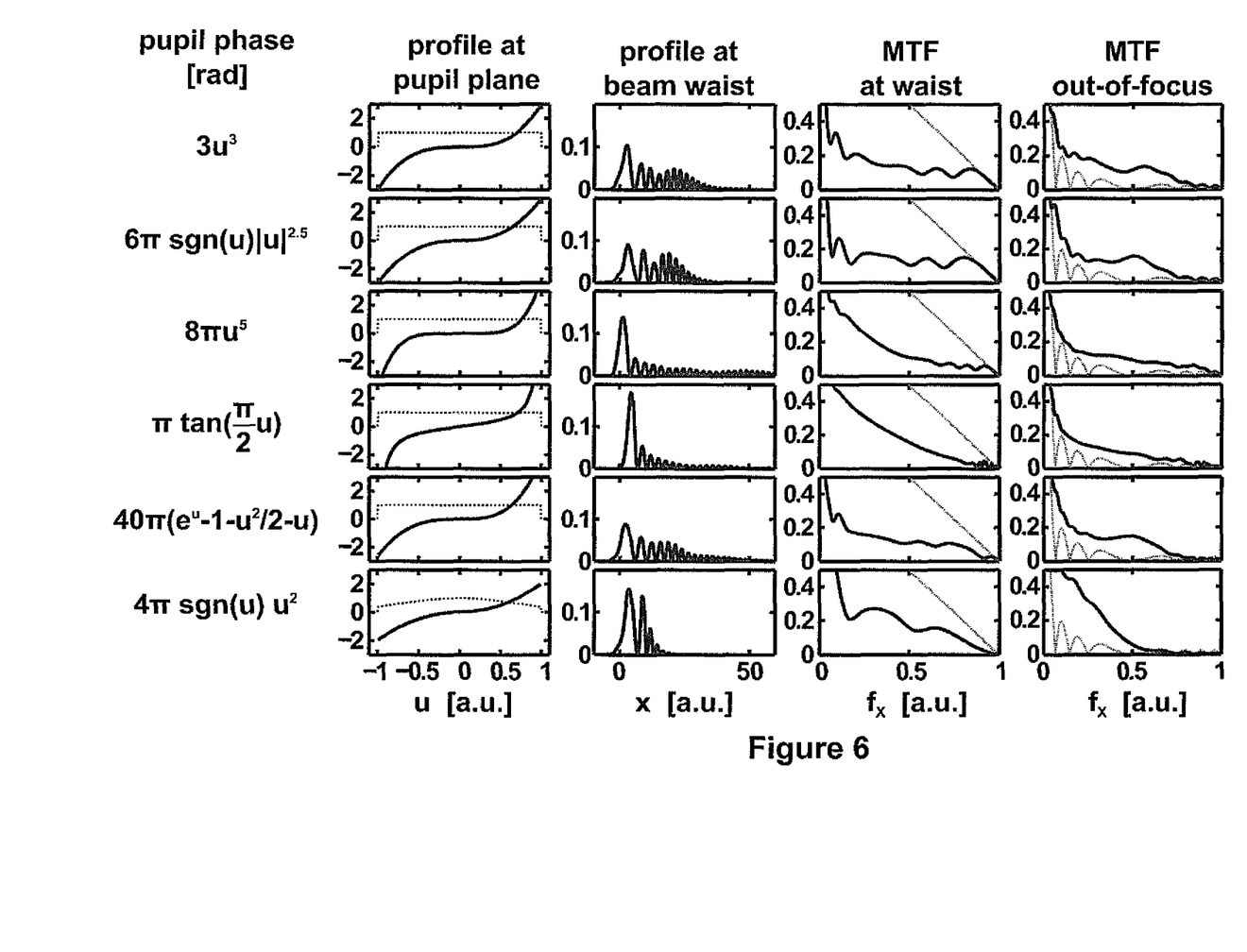
FIG. 6 shows various alternative asymmetric light sheet types that can be used to extend the imaging volume of a light sheet microscope.

Digital post-processing is often hampered by a limited knowledge of the point-spread function, which can give rise to an image shift and ringing artifacts, for example when the distance to the focal plane of the Airy beam is uncertain. However, this is not an issue in light sheet microscopy, because the side-on detection means that a direct relationship exists between the propagation distance of the light sheet and the position on the detector array. Linear deconvolution can therefore accurately correct both the amplitude and phase of the optical transfer function, effectively cancelling the curvature of the Airy beam light sheet, as well as any residual phase artifacts originating from the finite aperture used to create the Airy beam. Furthermore, the accurate knowledge of the point-spread function means that the light sheet does not have to be propagation invariant, it is sufficient that the MTF has no zeros for the required spatial frequencies and field-of-view. By consequence, a large family of asymmetric beams can be used to extend the field-of-view of a light sheet microscope. Several examples are depicted in FIG. 6.

Figure 4:
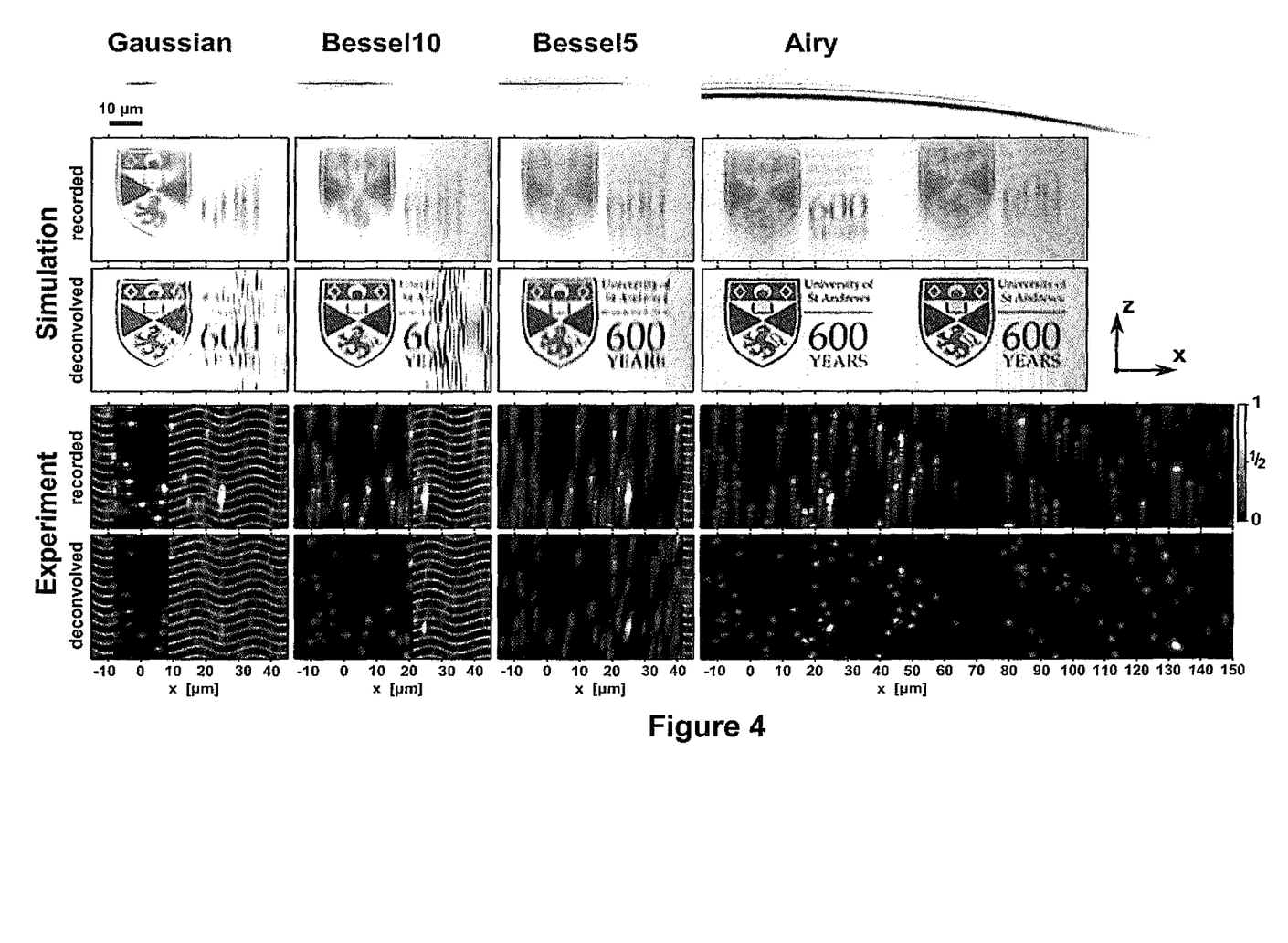
FIG. 4 show the same four different light sheets together with simulated and experimental images obtained with the respective light sheet types. The images show y-axis maximum-intensity projections for both the recorded raw data and the deconvolved data volumes.

FIG. 4 shows experimental and simulated data for light sheet illumination with various beam types. The beams are shown in the top row. Maximum intensity projections along the y-axis are shown for (left to right) the apertured Gaussian, two Bessel beam light sheets, respectively with an annular aperture width of 10% and 5% of the aperture radius, and the Airy beam light sheet. Row 2 shows the simulation of the light sheet microscope performance with the same parameters as used in the experiments. Row 3 shows the deconvolution of the simulated data. Row 4 shows the experimental data for a PDMS sample containing fluorescent microspheres. Row 5 shows the deconvolution of the experimental data. All images have the same scale and coordinate system in which the focal plane is at x≡0. For clarity, false-colour coding is used for the experimental images and light sheet profiles (inverted scale).

FIG. 4 demonstrates the high resolution and large field-of-view that can be obtained using the Airy beam light sheet with respect to conventional and Bessel beam illumination along the x-axis, for the conventional Gaussian light sheet. For conventional light sheet microscopy, the fluorescent beads cannot be resolved beyond 10 μm from the light sheet waist. Further away from the focal plane, nulls in the MTF (cf. FIG. 3*b*) lead to an irrevocable contrast loss and the consequent deconvolution artifacts. The Bessel beam light sheets effectively extend the field-of-view to 20 μm or 40 μm, approximately inversely dependent on the annular width if the aperture used to create the beam. The abrupt loss of resolution outside this region can be understood by considering the beam intensity profiles depicted in the top row of FIG. 4. At approximately 20 μm and 40 μm it can be seen how the on axis intensity decreases rapidly. At this point, due to the difference in optical path length between the inner and outer edge of the annular aperture, destructive interference leads to a degradation of the beam. A reduction of the annular width leads to an increased field-of-view.

However, it can also be noted that this has an adverse effect on the resolution. This can be seen more quantitatively by comparing the Bessel beam MTF curves shown in FIG. 3.

In contrast to the Bessel beams, the same sample imaged with the Airy light sheet has a field-of-view that covers the complete region of interest, while at the same time maintaining a high axial resolution throughout the full field-of-view. Moreover, 4D tracking of a single fluorophore is possible with lower peak power since, due to the side lobes of the Airy light sheet, useful signal can be collected over multiple frames. Fluorescence saturation, bleaching and photo damage are therefore less likely in comparison to conventional or Bessel beam light sheet imaging. The use of an Airy light sheet can thus extend the usable lifetime of the fluorophores.

Figure 5:
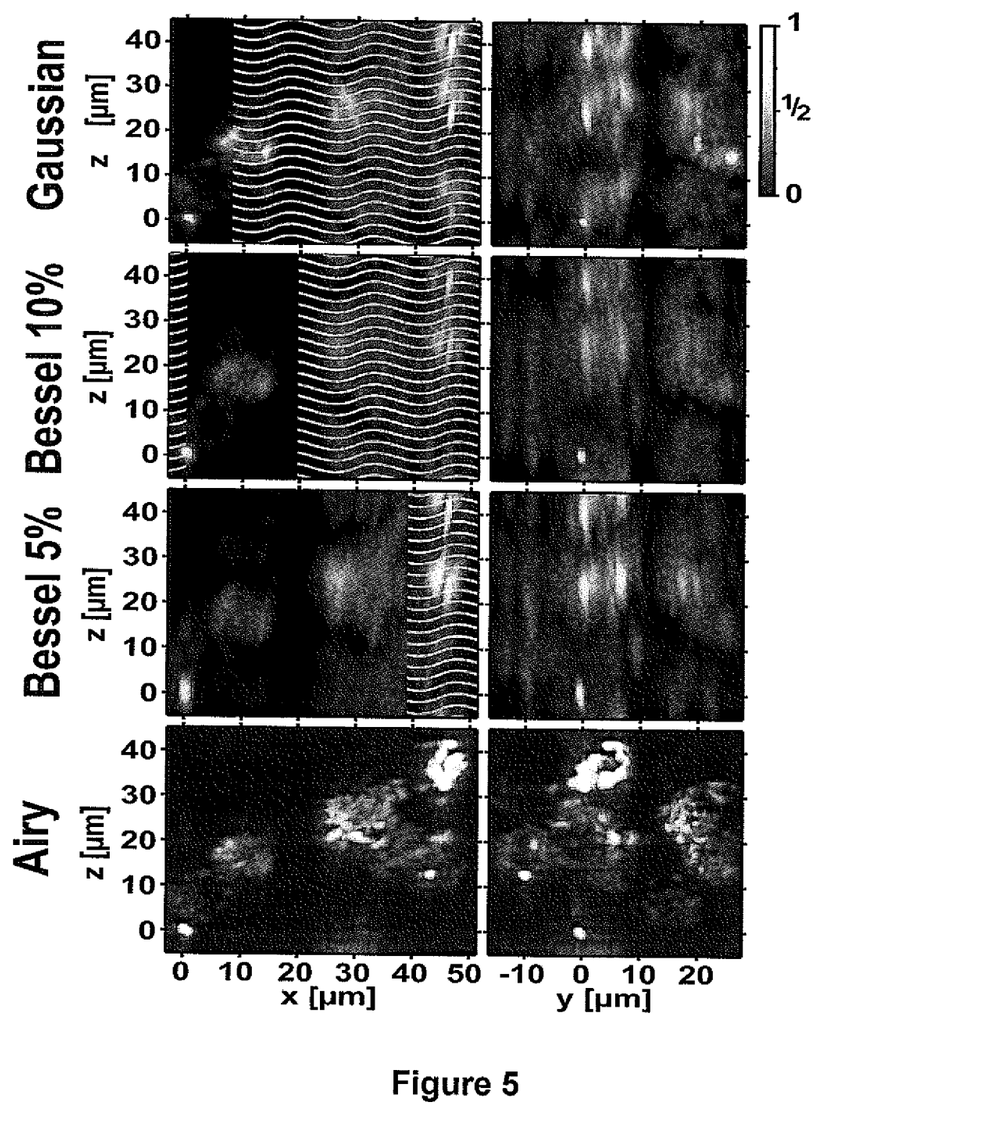
FIG. 5 shows the fluorescent mitochondria of a cluster of human embryonic kidney cells imaged with various light sheets.

The applicability of the technique has been further demonstrated for biological samples by imaging human embryonic kidney cells suspended in agarose gel. To enable a resolution comparison, the cells were transfected to express the fluorescent protein DsRed in the mitochondria. In-situ wavefront correction was achieved using fluorescent microspheres pre-mixed into the agarose gel as fluorescent probes near the cells of interest. FIG. 5 shows a cluster of cells spread out over a volume inaccessible by conventional light sheet microscopy. Both x and y axis views are shown for all beams. While both Bessel beam light sheet can be seen to resolve more cells than the apertured Gaussian light sheet, only Airy beam light sheet microscopy can resolve all cells, and do so with high resolution.

FIG. 6 shows examples of different asymmetric light sheets that can be used for extended volume light sheet imaging. Left column: equation of the phase modulation, specified in radians, as function of the normalised pupil coordinate, u. Both parabolic beams and Airy beams have a cubic phase profile as described by the equation on the first row. The second and third rows show a fractional and a fifth order exponent, respectively. The fourth and fifth rows show a goniometric and exponential function with an infinite number of components in its Taylor expansion. As a final example, the sixth row shows a second order polynomial phase modulation combined with a Gaussian amplitude modulation.

Column 2 of FIG. 6 shows the phase (solid thick blue line, [units of wavelength]), and transmission amplitude (dashed black line, arbitrary units). The amplitude of the beams is not modulated except for the last type which for the purpose of demonstration is modulated with a Gaussian apodisation. Column 3 of FIG. 6 shows the intensity profile of the beam (and therefore light sheet) due to the corresponding modulation. Column 4 shows the MTF at the waist for the respective light sheet (thick solid blue line), and the MTF of the traditional aperture Gaussian light sheet for comparison (dashed red line). Column 5 shows the out-of-focus MTF corresponding to a defocus introducing an optical path difference of two wavelengths ($W_{20}=2\lambda$). Unlike for the traditional aperture Gaussian MTF, no nulls are seen in the MTF of the modulated light sheets, and the contrast is considerably higher at the out-of-focus plane for most of the spatial frequencies. Even if this list is not exhaustive, it is clear that the light sheet used to extend the high resolution imaging volume needs not be restricted to the Airy beam light sheet. Specific applications or implementations may benefit from an alternative asymmetric light sheet.

A skilled person will appreciate that variations of the disclosed arrangements are possible without departing from the scope of the invention. Although the invention is described specifically with reference to selective plane illumination microscopy, it could equally be applied to any arrangement that uses a sheet of light, for instance for imaging, spectroscopy, such as fluorescence or Raman spectroscopy, or excitation or exerting optical forces, such as trapping or guiding. Equally, types of radiation other than the optical radiation described herein could be used for example, millimeter wave, terrahertz, x-ray, radar or acoustic. Accordingly the above description of the specific embodiment is made by way of example only and not for the purposes of limitation. It will be clear to the skilled person that minor modifications may be made without significant changes to the operation described.

The invention claimed is:

1. A light sheet optical system comprising:
   a light sheet generating element; and
   a modulating element, wherein the light sheet generating element and the modulating element are configured to create one or more of a non-diffractive, quasi non-diffractive, or propagation invariant asymmetric light sheet having an asymmetric intensity profile in a direction transverse to a direction of propagation of the asymmetric light sheet, wherein the modulating element is positioned in an illumination path of a light sheet optical system before or after the light sheet generating element, or wherein the modulating element is integrated with the light sheet generating element.

2. The light sheet optical system as claimed in claim 1, wherein the modulating element is configured to create one or more of a non-diffractive, quasi non-diffractive, or propagation invariant asymmetric beam that has an asymmetric intensity beam profile in a direction transverse to a direction of propagation of the beam, and wherein the light sheet generating element is configured to form the one or more of the non-diffractive, quasi non-diffractive, or propagation invariant asymmetric light sheet using the one or more of the non-diffractive, quasi non-diffractive, or propagation invariant beam.

3. The light sheet optical system as claimed in claim 2, wherein the one or more of the non-diffractive, quasi non-diffractive, or propagation invariant asymmetric beam has a Fourier transform that includes a phase term which has a second or higher order polynomial.

4. The light sheet optical system as claimed in claim 2, wherein the one or more of the non-diffractive, quasi non-diffractive, or propagation invariant asymmetric beam has a Fourier transform which contains a third or higher order component in the Taylor expansion of the phase modulation.

5. The light sheet optical system as claimed in claim 2, wherein the one or more of the non-diffractive, quasi non-diffractive, or propagation invariant asymmetric beam is self-healing or self-repairing.

6. The light sheet optical system as claimed in claim 2, wherein the one or more of the non-diffractive, quasi non-diffractive, or propagation invariant asymmetric beam results in no or a minimal number of zeros in the modulation transfer function of the light sheet optical system.

7. The light sheet optical system as claimed in claim 2, wherein the modulating element comprises a static or dynamic spatial light modulator or other static or dynamic diffractive optical element for forming the one or more of the non-diffractive, quasi non-diffractive, or propagation invariant asymmetric beam.

8. The light sheet optical system as claimed in claim 2, further comprising a beam scanning arrangement for moving or positioning the one or more of the non-diffractive, quasi non-diffractive, or propagation invariant asymmetric light sheet to capture images at different positions throughout a sample volume.

9. The light sheet optical system as claimed in claim 8, further comprising a detection objective and one or more optical elements which are configurable to ensure that a focal plane of the detection objective coincides with the one or more of the non-diffractive, quasi non-diffractive, or propagation invariant asymmetric light sheet.

10. The light sheet optical system as claimed in claim 2, further comprising:
a detector array or camera; and
a phase modulator in a detection path between the one or more of the non-diffractive, quasi non-diffractive, or propagation invariant asymmetric light sheet and the detector array or camera, wherein the detector array or camera and the phase modulator are configured for forming a volume image using light detected from multiple light surfaces formed by the one or more of the non-diffractive, or quasi non-diffractive, or propagation invariant asymmetric light sheet.

11. The light sheet optical system as claimed in claim 2, wherein the system is arranged to used single photon excitation.

12. The light sheet optical system as claimed in claim 2, wherein the one or more of the non-diffractive, quasi non-diffractive, or propagation invariant beam comprises an Airy beam.

13. The light sheet optical system as claimed in claim 2, wherein the one or more of the non-diffractive, quasi non-diffractive, or propagation invariant asymmetric beam has a Fourier transform that includes a phase term which has a fractional exponent of 2.5 or a cubic exponent.

14. The light sheet optical system as claimed in claim 2, further comprising a sample translation stage for moving or positioning a sample relative to the one or more of the non-diffractive, quasi non-diffractive, or propagation invariant asymmetric light sheet to capture images at different positions throughout a volume of the sample.

15. The light sheet optical system as claimed in claim 1, wherein the light sheet generating element is configured to form a symmetric light sheet having a symmetric intensity profile in the direction transverse to a direction of propagation of the symmetric light sheet; and the modulating element is configured to convert the symmetric light sheet to one or more of the non-diffractive, quasi non-diffractive, or propagation invariant asymmetric light sheet having the asymmetric intensity profile in the direction transverse to the direction of propagation of the asymmetric light sheet.

16. The light sheet optical system as claimed in claim 15, wherein the modulating element comprises a phase modulation element which is in an illumination path on which the symmetric light sheet propagates.

17. The light sheet optical system as claimed in claim 16, wherein the phase modulating element provides a cubic phase modulation.

18. The light sheet optical system as claimed in claim 15, wherein the modulating element comprises a mask in the illumination path on which the symmetric light sheet propagates.

19. The light sheet optical system as claimed in claim 1, wherein the system is one or more of a light sheet imaging system; a spectroscopy system; a microscopy system; and a system for exerting an optical force on a particle.

20. The light sheet optical system as claimed in claim 19, wherein the system is a Raman spectroscopy system.

21. The light sheet optical system as claimed in claim 19, wherein the particle comprises one or more of an inert or a biological particle, and a cell.

22. The light sheet optical system as claimed in claim 19, wherein the system is an optical trapping system or an optical guiding system.

* * * * *